US00PP10311P

United States Patent [19]

Tachibana

[11] Patent Number: Plant 10,311

[45] Date of Patent: Mar. 31, 1998

[54] VERBENA PLANT NAMED 'SUNVP-SU'

[75] Inventor: Ryuichi Tachibana, Yamato, Japan

[73] Assignee: Suntory Limited, Osaka, Japan

[21] Appl. No.: 746,563

[22] Filed: Nov. 13, 1996

[51] Int. Cl.[6] ..... A01H 5/00

[52] U.S. Cl. ..... Plt./87

[58] Field of Search ..... Plt./87

[56] References Cited

U.S. PATENT DOCUMENTS

| | | | |
|---|---|---|---|
| P.P. 8,995 | 11/1994 | Tachibana et al. | Plt./87 |
| P.P. 9,014 | 12/1994 | Tachibana et al. | Plt./87 |
| P.P. 9,059 | 2/1995 | Tachibana et al. | Plt./87 |
| P.P. 9,085 | 3/1995 | Tachibana et al. | Plt./87 |
| P.P. 9,121 | 4/1995 | Tachibana et al. | Plt./87 |
| P.P. 9,411 | 12/1995 | Tachibana et al. | Plt./87 |

*Primary Examiner*—James R. Feyrer
*Assistant Examiner*—Elizabeth C. Kemmerer
*Attorney, Agent, or Firm*—Morgan & Finnegan; Eugene Moroz; Mary J. Morry

[57] ABSTRACT

Disclosed herein is a Verbena plant having a spread growth habit, long stems and a broad spreading area of plant flowers. The plant has abundant branching, plentiful number of flowers in a spike, and a great profusion of blooms. The blooming period is late April to November and flowering duration is long. The whole bush remains in bloom for a considerable period of time. The flower size is large and the petal color of the flower is a vivid red color. The plant has high tolerances to cold and heat, high resistance to pests and diseases, particularly powdery mildew, and high resistance to rain.

2 Drawing Sheets

BACKGROUND OF THE VARIETY

The present invention relates to a new and distinct variety of Verbena plant obtained from crossing a "Showtime" (♀) and a wild type of Verbena plant *Verbena peruviana* (L.) (♂) native to Brazil.

The Verbena is a very popular plant and is used for flower bedding and potting in the summer season. There are only a few varieties of the verbena plant which have a spread growth habit, much branching, many number of flowers in a spike and which have a high resistance to rain, heat, cold, and diseases. Accordingly, this invention was aimed at obtaining a new variety having a slightly erected spread growth habit, strongly branching, many number of flowers in a spike, large diameter flowers, high tolerance to heat and cold, and resistance to diseases and pests, and also having a vivid red color petal.

The new variety of verbena plant according to this invention originated from crossing of "Showtime" (♀) and a wild type of verbena plant *Verbena peruviana* (L.) (♂) native to Brazil.

First of all, 35 seedlings were obtained from crossing "Showtime", which has red flower petals, as the female parent and a wild type of Verbena plant, which has red flower petals, as pollen parent in the spring of 1989. From this crossing 5 seedlings were selected in view of spread growth habit and propagated by cutting, and then grown in a trial by flower bedding and planter from in the spring of 1990. And then 2 seedlings which were selected from these 5 seedling were carried out in a trial by flower potting and bedding from in the spring of 1991 and the botanical characteristics of 2 seedlings were then examined, using similar varieties "Showtime" and "Derby Scarlet" for comparison. Finally only one plant was selected. As a result, it was concluded that this Verbena is distinguishable from any other variety, whose existence is known to us, sufficiently uniform and stable in its characteristics, then this new variety of Verbena plant was named "SUNVP-SU".

In the following description, the color-coding is in accordance with the Horticultural Colour Chart of The Royal Horticultural Society, London, England (R.H.S. Colour Chart), and the Inter-Society Color Council-Nation Bureau of Standard Color Name (I.S.C.C.-N.B.S. Color Name). A color chart based on The Japan Color Standard for Horticultural Plant (J.H.S. Color Chart) is also added for reference.

The "Showtime" used as female parent in the obtaining of this new variety "SUNVP-SU", is bred by the T&M Corp., ENGLAND and are on the market. The "Showtime" series includes red flower petals, pink flower petals, purple flower petals and white flower petals, and the like. The main botanical characteristics of "Showtime" are as follows.

Plant:
- *Growth habit.*—Semi-erect.
- *Plant height.*—20–25 cm.
- *Plant extension.*—20–30 cm.

Stem:
- *Diameter.*—2.0–2.5 mm.
- *Anthocyanin pigmentation.*—Absent.
- *Branching.*—Few.
- *Pubescence.*—Medium.
- *Length of internode.*—1.6–2.0 cm.

Leaf:
- *Phyllotaxis.*—Opposite.
- *Shape of blade.*—Hastate.
- *Length.*—5.0–6.0 cm.
- *Width.*—1.5–2.0 cm.
- *Depth of incision.*—Shallow.
- *Color.*—Dark olive green (R.H.S. 137B, 147A, JHS 3707).
- *Pubescence.*—Medium.

Flower:
- *Facing direction.*—Upward.
- *Outward curvature of petal.*—None.
- *Diameter.*—1.5–2.0 cm.
- *Height.*—20–25 mm.
- *Color.*—Deep reddish orange (R.H.S. 46B, JHS 0708).
- *Color intensity.*—Absent.
- *Overlapping of petals.*—Closed.
- *Spike.*—40–50 mm in length; and 40–50 mm in diameter.

*Calyx.*—1.0–1.5 cm in length.
*Anthocyanin pigmentation of calyx limb.*—Absent.
*Peduncle.*—2–3 mm in thickness; and 5.0–7.0 cm in length.
*Number of flowers.*—Medium (9–12).
*Reproductive organs.*—1 pistil and 5 stamens.
*Flower fragrance.*—Absent.
*Flowering duration.*—Medium.

Physiological and ecological characteristics: Moderate resistance to diseases and pests, medium tolerances to heat and cold.

The pollen parent used in the obtaining of this new variety "SUNVP-SU" was a wild type of verbena native to South Brazil and *Verbena peruviana* (L.). This wild type of verbena plant is presently maintained at the Plant Biotechnology Laboratory of SUNTORY Ltd., residing at 863-1, Aza-Iketani, Oomori-cho, Youkaiti-shi, Shiga-ken, Japan. The main botanical characteristics of this pollen parent are as follows.

Plant:
*Growth habit.*—Slightly erected spread.
*Plant height.*—5–8 cm.
*Plant extension.*—100–150 cm.

Stem:
*Diameter.*—2.0–3.0 mm.
*Anthocyanin pigmentation.*—Present.
*Branching.*—Medium.
*Pubescence.*—Medium.
*Length of internode.*—3.0–5.0 cm.

Leaf:
*Phyllotaxis.*—Opposite.
*Shape of blade.*—Narrow lanceolate.
*Length.*—3.0–4.0 cm.
*Width.*—2.0–2.5 cm.
*Depth of incision.*—Shallow.
*Color.*—Moderate olive green (R.H.S. 146A, JHS 3509).
*Pubescence.*—Few.

Flower:
*Facing direction.*—Upward.
*Outward curvature of petal.*—Slightly curved.
*Diameter.*—1.5–2.0 cm.
*Height.*—15–20 mm.
*Color.*—Vivid reddish orange (R.H.S. 40A–40B, JHS 0706).
*Color intensity.*—Absent.
*Overlapping of petals.*—Separate.
*Spike.*—30–40 mm in length; and 40–50 mm in diameter.
*Calyx.*—1.0–1.2 cm in length.
*Anthocyanin pigmentation of calyx limb.*—Present.
*Peduncle.*—1.2 mm in thickness; and 5.0 cm in length.
*Number of flowers.*—Plentiful (13–15).
*Reproductive organs.*—1 pistil and 5 stamens.
*Flower fragrance.*—Absent.
*Flowering duration.*—Short.

Physiological and ecological characteristics: High resistance to diseases and pests, high tolerance to heat and moderate tolerance to cold.

This new variety of verbena plant "SUNVP-SU" was asexually reproduced by cutting at the aforementioned Plant Biotechnology Laboratory of SUNTORY Ltd., residing at 863-1, Aza-Iketani, Oomori-cho, Youkaiti-shi, Shiga-ken, Japan, and the homogeneity and stability thereof were confirmed.

SUMMARY OF THE VARIETY

This new variety of Verbena plant has slightly erected spread growth habit having long stems and broad spreading area of plant. The plant has abundant branching and plentiful numbers of flowers in a spike, and great profusions of blooms. The Blooming period is late April to November and the flowering duration is long. And whole bush remains in bloom for a considerable period of time. The flower size is large and the petal color of the flower is a vivid red color. The plant is highly tolerant to cold and heat, and has a high resistance to pests and diseases, particularly powdery mildew.

DESCRIPTION OF THE VARIETY

Figure 1:
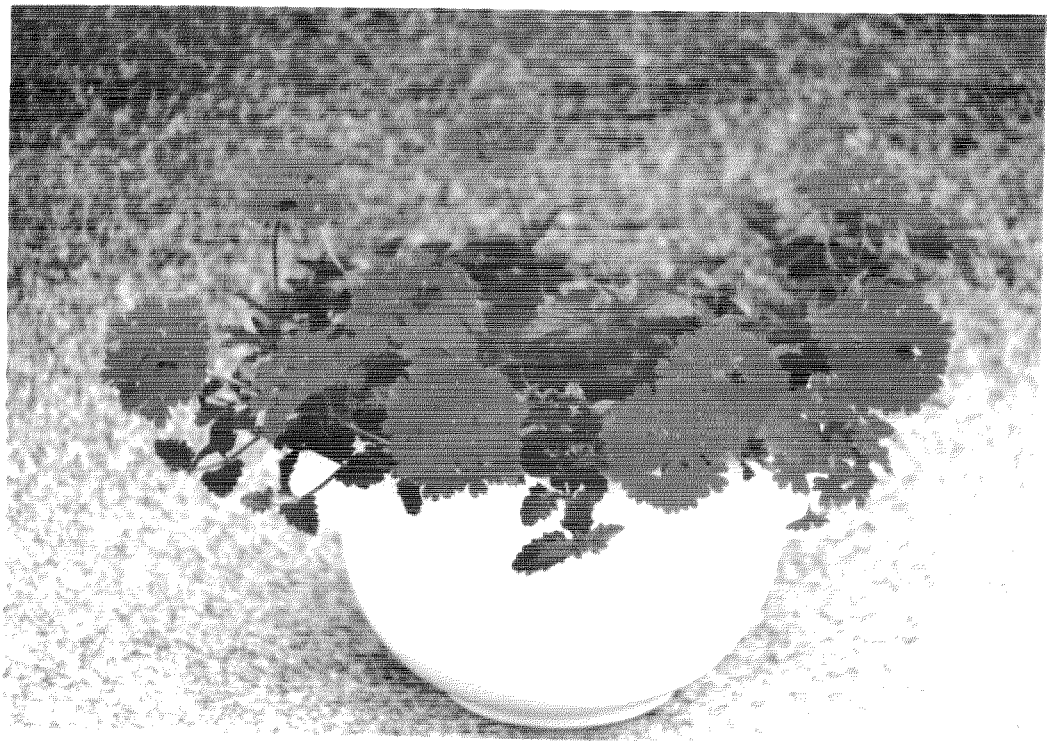
FIG. 1 is a photograph giving a partial view of the new variety of verbena plant planted in a flower pot.
Figure 2:
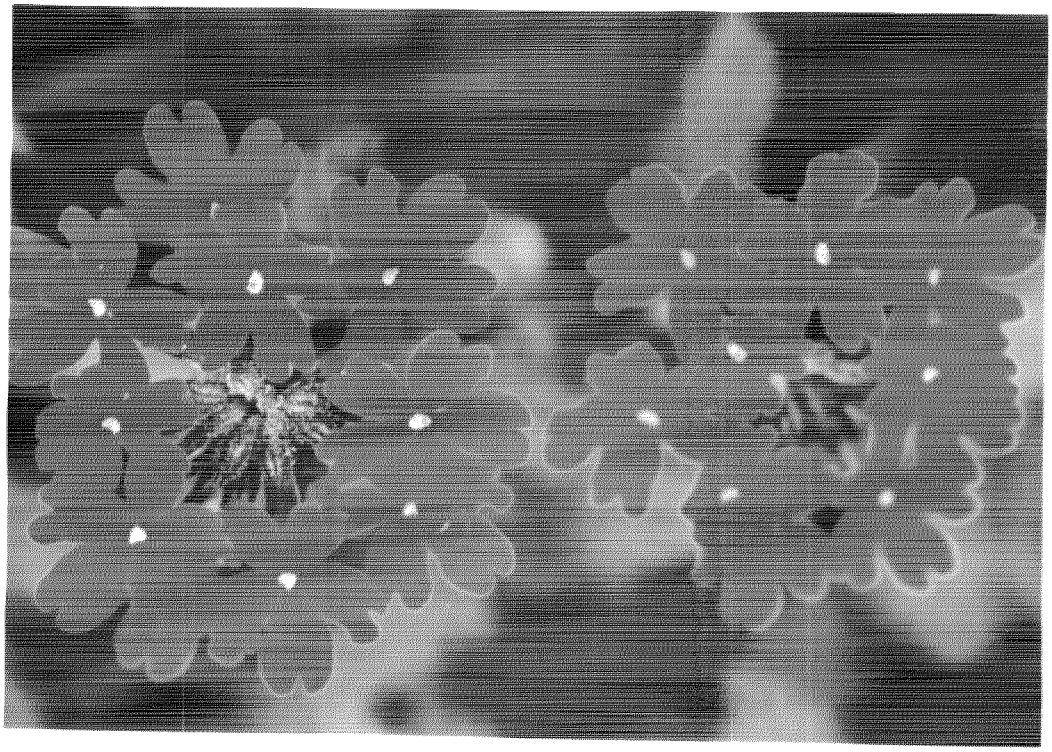
FIG. 2 is a photograph of flowers of the new variety of verbena plant.

The botanical characteristics of the new and distinct variety of Verbena plant, "SUNVP-SU" are as follows.

Plant:
*Growth habit.*—Slightly erected spread.
*Plant height.*—20–30 cm.
*Plant extension.*—30–50 cm.
*Growth.*—Very vigorous with abundant branching and great profusion of blooms; the whole bush remaining in bloom for a considerable period of time.

Stem:
*Diameter.*—2.0–3.0 mm.
*Anthocyanin pigmentation.*—Present.
*Branching.*—Abundant.
*Pubescence.*—Medium.
*Length of internode.*—3.0–6.0 cm.

Leaf:
*Phyllotaxis.*—Opposite.
*Shape of blade.*—Hastate.
*Length.*—4.0–6.0 cm.
*Width.*—2.0–3.0 cm.
*Depth of incision.*—Shallow.
*Color.*—Dark olive green (R.H.S. 137B, JHS 3708).
*Pubescence.*—Few.

Flower:
*Facing direction.*—Upward.
*Outward curvature of petal.*—Slightly curved.
*Diameter.*—2.0 cm.
*Height.*—15–20 mm.
*Color.*—Vivid red. (R.H.S. 52A, JHS 0407).
*Color intensity.*—Absent.
*Overlapping of petals.*—Separate.
*Spike.*—30–40 mm in length; and 50–70 mm in diameter.
*Calyx.*—1.0–1.5 cm in length.
*Anthocyanin pigmentation of calyx limb.*—Absent.
*Peduncle.*—2–3 mm in thickness; and 4.0–7.0 cm in length.
*Number of flowers.*—Plentiful (15–20).
*Reproductive organs.*—1 pistil and 5 stamens.
*Flower fragrance.*—Absent.
*Flowering duration.*—Long.

Physiological and ecological characteristics: High resistance to diseases and pests, particularly powdery mildew. High tolerances to heat and moderate tolerances to cold.

This new variety of verbena plant is most suitable for flower bedding and potting, particularly in planters, and is further excellent for ground cover.

The plant of this new variety, "SUNVP-SU" is presently planted and maintained at the Plant Biotechnology Laboratory of SUNTORY Ltd., residing at 863-1, Aza-Iketani, Oomori-cho, Youkaiti-shi, Shiga-ken, Japan.

I claim:

1. A new and distinct variety of Verbena plant, substantially as herein illustrated and described, characterized particularly as to novelty by (A) being a spread growth habit having long stems, (B) an abundant branching and plentiful number of flower in a spike and great profusion blooms, the whole bush remaining in bloom for a considerable period of time, (C) flower size is large and the petal color of flower is vivid red color, (D) a high resistance to rain, heat, drought, cold and pest.

* * * * *